US00PP09594P

United States Patent [19]

Buhler

[11] Patent Number: Plant 9,594

[45] Date of Patent: Jun. 25, 1996

[54] "PRETTY LADY" PEACH TREE

[76] Inventor: John A. Buhler, 41130 Road 48, Reedley, Calif. 93654

[21] Appl. No.: 377,982

[22] Filed: Jan. 25, 1995

[51] Int. Cl.[6] ..... A01H 5/00

[52] U.S. Cl. ..... Plt./43.2

[58] Field of Search ..... Plt./43.2

[56] References Cited

U.S. PATENT DOCUMENTS

P.P. 8,956 10/1994 Peters ..... Plt./43.2

*Primary Examiner*—James R. Feyrer
*Attorney, Agent, or Firm*—Worrel & Worrel

[57] ABSTRACT

A new and distinct variety of peach tree which is somewhat remotely similar to the "Summer Lady" peach tree (U.S. Plant Pat. No. 5,865) of which it is a sport, but from which it is distinguished by producing fruit which are mature for harvesting and shipment approximately August 5 to August 20 in the San Joaquin Valley of central California which is of an excellent quality having an exceptional sweet flavor, and a firm flesh.

1 Drawing Sheet

BACKGROUND OF THE NEW VARIETY

The present invention relates to a new and distinct variety of peach tree, which will hereinafter be denominated varietally as the "Pretty Lady" peach tree and, more particularly, to a peach tree which produces freestone fruit which are mature for commercial harvesting and shipment approximately August 5 to August 20 in the San Joaquin Valley of central California.

Due to the market appeal therefor, a premium is placed on varieties of peach trees which produce fruit which is both of high skin coloration and sweet flavor as compared with other commercially available fruit. Where these attributes are present in combination with flesh which is very firm and thus excellently suited to commercial harvesting, packing and shipping practices, the variety may be of unusual value. The new variety of the present invention produces fruit which appears to be of excellent character in all of these respects. In addition, the fruit of the new variety is believed to be well suited to storage for extended periods of time due to the density of the flesh thereof. As such, the new variety of the instant invention appears to possess a very promising commercial potential.

ORIGIN AND ASEXUAL REPRODUCTION OF THE NEW VARIETY

The present variety of peach tree hereof was discovered by the inventor in 1987 in his orchard which is located in Reedley in the San Joaquin Valley of central California. The variety was discovered as a sport on a single branch located on the westerly side of a "Summer Lady" peach tree (U.S. Plant Pat. No. 5,865) in the orchard approximately 2 meters (6 feet) above ground level. Fruit and stability evaluations were conducted by the inventor in the succeeding years 1988, 1989 and 1990.

The new variety was first asexually reproduced at the inventor's direction in 1991 at Modesto, Calif. using bud grafts from the parent sport. The bud grafts were grafted onto 'Nemaguard' rootstock. The resulting asexually reproduced trees of the new variety were planted in 1992 on the inventor's property in Reedley. The inventor has, in succeeding years, observed the asexually reproduced trees of the new variety and confirmed that they are identical in all respects to the parent sport.

SUMMARY OF THE NEW VARIETY

The "Pretty Lady" peach tree is characterized by producing a freestone fruit of very high skin coloration and which are ripe for commercial harvesting and shipment approximately August 5 to August 20 in the San Joaquin Valley of central California. The new variety is most closely similar to the "Summer Lady" peach tree (U.S. Plant Pat. No. 5,865) of which it is a sport, but is distinguishable therefrom by the aforementioned ripening date. The fruit has an exceptionally good, sweet flavor. While the "August Lady" peach tree produces fruit maturing on or approximately August 5 in the San Joaquin Valley of central California, the fruit of the new variety is available for harvest over a much longer harvest period retaining its firmness over this much more extended period. During this extended period of fruit life while the fruit holds on the tree, the fruit retains its shipping and handling firmness and increases daily in fruit size, color and flavor.

BRIEF DESCRIPTION OF THE DRAWING

The accompanying drawing is a color photograph showing fruit of the new variety including a first in top plan view showing the stem cavity and shoulders thereof; a second in side elevation showing the suture area thereof; a third in side elevation rotated ninety degrees (90° ) from the suture area thereof; a fourth in bottom plan view showing the apex thereof; a fifth sectioned and laid open to expose the stone in the natural location thereof in one section and the pit well in the other section; and representative foliage and wood of the new variety.

DETAILED DESCRIPTION

Referring more specifically to the pomological details of this new and distinct variety of peach tree, the following has been observed under the ecological conditions prevailing at the orchard of origin which is located in Reedley, Calif. All major color code designations are by reference to the Maerz and Paul, *A Dictionary of Color,* First Edition, 1930, McGraw-Hill Book Co., Inc., New York, N.Y. Common color designations are also occasionally employed.

TREE

Generally:

*Size.*—Average, large to medium.

*Vigor.*—Vigorous. Equal in vigor to the "O'Henry" peach tree (U.S. Plant Pat. No. 2,964) and the "Elegant Lady" peach tree (U.S. Plant Pat. No. 4,399).

*Chilling requirements.*—Moderate requirements. Six hundred (600) hours at forty-five degrees Fahrenheit (45°) accumulated during the dormancy season.

*Figure.*—Moderate spreading of scaffold branches. Tree structure adapts well to the commercial and conventional open vase tree training systems employed in the fruit producing regions of the San Joaquin Valley of central California.

*Productivity.*—Flowering buds and flowers are abundant. Fruit set after petal fall is abundant. Excess fruit removal is essential to production of commercially marketable fruit. Excess fruit is removed when the young fruit attains the diameter of 26 mm (1 inch) to 35 mm (1⅜ inches). Specific fruit spacing on all fruit bearing parts is 10 cm (4 inches) to 15 cm (6 inches).

*Regularity of bearing.*—Regular. Selection is not subject to biannual bearing.

Trunk:

*Size.*—Medium and uniform.

*Diameter.*—13 cm (5⅛ inches).

*Circumference.*—46 cm (18 inches).

*Surface texture.*—Course checked.

*Color.*—Dark brown, grey flecking (8-C-12).

*Lenticels.*—Average, evenly disbursed. Length — 6 mm (¼ inch). Height — 3 mm (⅛ inch).

Branches:

*Size.*—Average 7 cm (2¾ inches).

*Surface texture.*—Medium to light check.

*Surface color.*—Light brown (7-A-12).

*Fruit bearing twigs.*—Current season, pale green (19-K-4). Two year twigs, light grey brown (8-L-8).

*Lenticels—numbers.*—Occur on branches older than three years. Average in count, 3 lenticels per square centimeter.

*Lenticels—size—length.*—Variable from 3 mm (⅛ inch) to 6 mm (¼ inch).

*Lenticels—size—height.*—1 mm (1/32 inch) to 3 mm (⅛ inch).

*Tree height.*—Average tree height in five year old orchard, 4 meters (11½ feet).

*Tree diameter.*—Average tree diameter (dripline at foliage), 2 meter (7 feet).

LEAVES

Size:

*Generally.*—Large.

*Average length.*—18 cm (6¾ inches).

*Average width.*—4.5 cm (1¾ inches).

*Average thickness.*—Average.

Form: Lanceolate with an acuminate apex. Apex is distinctly curved and twisted.

*Color—upwardly disposed surface.*—23 E 9.

*Color—downwardly disposed surface.*—22 I 6.

*Color—leaf vein.*—(18 E 1).

*Marginal form.*—Generally — low, uniform crenations.

*Leaf vein.*—Very pronounced.

*Leaf vein—thickness.*—Fine pronounced.

*Leaf margin.*—Undulate on the apex portion of the leaf.

Glandular characteristics: Reniform in type.

*Leaf glands—size.*—Medium to Small.

*Leaf glands—position.*—Glands occur on petiole at the basal leaf margin. Occasionally very small glands appear on the base of the leaf margin.

*Leaf glands—color.*—Pale green yellow (18 E 1).

*Stem glands.*—Mostly singular and doubles are on opposing sides of the petiole.

*Glands.*—Size—1 mm (1/32 inch) to 2 mm (1/16 inch).

Petiole:

*Size.*—Medium to small.

*Length.*—10 mm (⅜ inch).

*Width.*—2 mm (1/16 inch).

*Color.*—(18 E 1).

Stipules: Slender, early deciduous

FLOWERS

Flower buds: Abundant.

Size: Medium to large.

Form: Conic.

Bud scales: Pubescent. Grey pubescence.

Flowers:

*Generally.*—Flowers are showy type and profuse with color.

Petal:

*Form.*—Petals open to full surface. Petals — Broad with shallow cupping.

*Petals—margin.*—Uniform wavy margin on both sides of apex.

*Petal—base—color.*—Deep pink (2 J 7), slight pink lining from base.

*Petal apex.*—Broad, rounded, uniform.

*Petal apex—color.*—Pale pink (1 A 7).

Date of bloom: Feb. 27 to Mar. 6. Coincides with commercial peach varieties commonly grown in the San Joaquin Valley.

Pollen Pods: Anthers.

*Size.*—Large, approximately 1 mm (1/32 inch).

*Color.*—Yellow (9 K 6).

*Pollen.*—Abundant.

Flower stamens: Abundant, wide spread.

*Color.*—Deep pink (2 J 7).

*Length.*—Average 12 mm (½ inch) to 15 mm (⅝ inch).

Pistil:

*Length.*—Average 12 mm (½ inch) to 15 mm (⅝ inch).

*Color.*—Pale yellow (9 B 1).

Fertility: The inventory of this variety has isolated branches of flower buds from other sources of pollen to determine self fruitfulness. The results indicate this new variety to be self fruitful.

FRUIT

Maturity when described: Ripe for commercial harvesting and shipment approximately August 5 to August 20 in Reedley in the San Joaquin Valley of central California.

Size:

*Generally.*—Fruit size is uniform over entire fruit bearing area of the tree.

*Average diameter in the axial plane.*—78 mm (3⅛ inches).

*Average diameter in the suture plane.*—72 mm (2⅞ inches).

*Average diameter transverse to the suture plane.*—78 mm (3⅛ inches).

Form:

*Uniformity.*—Nearly globus in all dimensions.

*Symmetry.*—Two halves are of equal form.

*Suture—generally.*—A very thin suture line is present extending from base to apex. On rare occasion, slight callous tissue is observed near the apex.

*Ventral surface—generally.*—Both sides at the suture are equal. Indentation of the suture line is not present.

Stem cavity:

*Generally.*—Medium, generally shallow and evenly flared.

*Width.*—27 mm (1⅛ inches).

*Depth.*—16 mm (⅝ inch).

*Length.*—32 mm (1¼ inches).

*Form.*—Generally oval.

Stem:

*Generally.*—Long and thick.

*Thickness.*—3 mm (⅛ inch).

*Length.*—10 mm (⅜ inch).

*Hilum.*—Attachment to hilum is small.

*Color.*—Light green (20 K 3).

*Base—generally.*—Broad, round and smooth.

*Apex—shape.*—Smooth, rounded.

Pistil point: Strongly oblique. Slight point.

*Size.*—Generally 3 mm (⅛ inch).

Skin:

*Thickness.*—Medium on all surfaces.

*Texture.*—Moderately thick and uniform, tenacious to flesh on all surfaces.

*Tendency to crack.*—None.

*Blush color.*—For the skin surface of fruit which is exposed to direct sunlight, about sixty percent (60%) thereof is (3 L 10).

*Ground color.*—(10 K 2). Generally covered by blush. Represented by about ten percent (10%) of overall color of fruit.

Flesh:

*Flesh color.*—Apricot yellow (9 K 5). Uniform color from pit cavity to skin.

*Surface of pit cavity.*—(3 K 6). Red pigment radiates from entire pit cavity. The red pigment extends outward from the pit cavity into the flesh. non-uniform extension of red color 3 mm (⅛ inch) near base of pit cavity to 6 mm (¼ inch) near apex of pit cavity. Red color extends nearly to the pistil point.

*Juice production.—Average — Distinct, pronounced, not watery.*

*Flavor.*—Well balanced, sweet flavor commonly associated with peach flavor. Slightly acid. To determine soluble solids in the fruit of the new variety, a refractometer was used. Fruit samples were taken from four locations of the tree. Fruit maturation at firm ripe is suitable for harvest and produced Brix readings of 12, 13, 12 and 13, respectively. Four days thereafter, firm ripe fruit from the same four locations produced Brix readings of 13, 14, 13 and 14, respectively. Fruit of the new variety produced tested eleven days after the first test were firm ripe and suitable for commercial harvest. They produced Brix readings of 12, 14, 13 and 14, respectively. Fruit specimens thirteen days after the first test were soft ripe and produced Brix readings of 14, 16, 14 and 16, respectively. All Brix readings were made at the respective orchard sites.

*Aroma.*—Distinct and pronounced.

*Texture.*—Very firm, dense, fine. Melting to creamy texture when soft ripe.

Fibers—numbers.—Very few, obscure.

*Fibers—texture.*—Very fine.

*Ripening.*—Ripens uniform over entire flesh area.

*Pubescence.*—Very short and dense.

*Eating quality.*—Exceptionally good flavor. Noted flavor of fruit harvested in firm flesh and matured to delightful flavor at distant commercial markets.

Stone:

*Attachment.*—Freestone.

*Fibers.*—Present on ventral edge.

*Fibers.—numbers.*—Commonly two, occasionally three, attached to the basal end on both or just one side.

*Basal end fibers—size.*—5 mm (¼ inch).

*Secondary fibers—size.*—3 mm (⅛ inch).

*Size—length.*—35 mm (1⅜ inches).

*Size—width.*—26 mm (1 inch).

*Size—thickness.*—20 mm (¾ inch).

*Form.*—Generally — Irregular.

*Apex.*—Shape — Abrupt curve to point on dorsal edge, Gentle curve.

*Color.*—Dry, clean and free of all fruit parts.

*Color—base ridges.*—Uniform (5 H 11).

*Color—apex ridges.*—Uniform (5 H 11).

*Base—Shape.*—Fine ridges, irregular taper to hilum.

*Sides.*—Generally — Equal.

*Hilum.*—Finely serrated over circumference.

*Hilum—length.*—Length in line with suture 5 mm (¼ inch).

*Hilum—width.*—Perpendicular to suture 3 mm (⅛ inch).

*Ridges.*—Moderately ridged on base. Deeply ridges on midsection and apex. Ridges on apex extend from midsection to apex; equal on both sides. Ridges on midsection and base are deeply pitted and irregularly attached. Base of stone is finely pitted near hilum.

*Dorsal edge.*—A single groove extending from base of apex. Groove on base to midsection is coarsely lined by ridges on equal sides. Groove from midsection to apex is a single uniform uninterrupted groove line.

*Tendency to split.*—None observed.

Use: Fresh fruit consumption.

Keeping quality: The fruit of the new variety is noteworthy in that it has high flesh density and retains its firmness over an unusually lengthy period of time when compared with the fruit of other varieties. Refractometer readings appear to indicate that the fruit flesh at a Brix reading of 12 has reached shipping and marketing maturation. Fruit left on the tree eight to eleven days longer has retained a firmness suitable for handling while having gained in size and flavor. The presence of high soluble solids indicates that the fruit will achieve maximum flavor at the market destination. The firmness permits the fruit to be harvested at optimum maturity.

Resistance to disease: The new variety has not been observed to show either unusual susceptibility or resistance to diseases, pests and disorders common to orchards of the central San Joaquin Valley of California.

Harvesting: Fruit harvested by traditional means common to the fruit growing area. Fresh fruit peaches are all hand picked in the orchard.

Shipping and handling qualities: The overall and general observation of this peach selection is favorable and superior in all aspects of growing the trees in the orchard. The cultural maintenance of the orchard is normal and grower friendly. The fruit is firm, colorful and matures evenly over the fruit bearing area. Handling the picked fruit in the conventional manner from the orchard through the packing house has been without special care and with excellent pack outs. The fruit has been transported to markets throughout the United States arriving in excellent condition.

Although the new variety of peach tree possesses the described characteristics noted above as a result of the growing conditions prevailing near Reedley, Calif. in the central part of the San Joaquin Valley of California, it is to be understood that variations of the usual magnitude and characteristics incident to changes in growing conditions, irrigation, fertilization, pruning, pest control, climatic variation and the like are to be expected.

Having thus described and illustrated my new variety of peach tree, what I claim as new and desire to be secured by Plant Letters Patent is:

1. A new and distinct variety of peach tree substantially as illustrated and described which is somewhat remotely similar to the "Summer Lady" peach tree (U.S. Plant Pat. No. 5,865) of which it is a sport, but from which it is distinguished by producing fruit which are mature for commercial harvesting and shipment approximately August 5 to August 20 in the San Joaquin Valley of central California and which have an excellent sweet flavor and firm flesh.

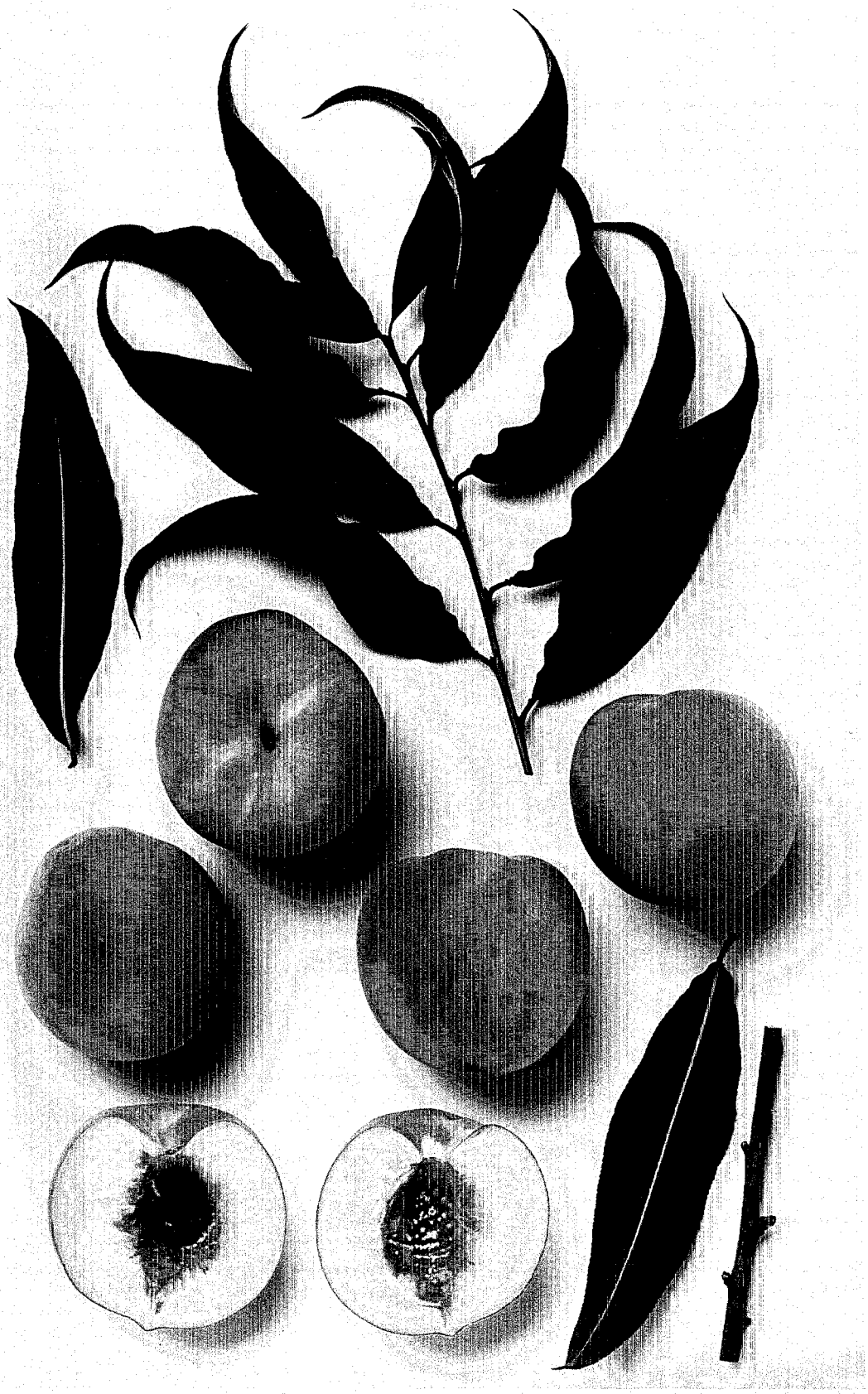

* * * * *